US009700708B2

(12) United States Patent
Doyle, III et al.

(10) Patent No.: US 9,700,708 B2
(45) Date of Patent: Jul. 11, 2017

(54) MAINTAINING MULTIPLE DEFINED PHYSIOLOGICAL ZONES USING MODEL PREDICTIVE CONTROL

(71) Applicants:Francis J. Doyle, III, Santa Barbara, CA (US); Benyamin Grosman, Northridge, CA (US); Eyal Dassau, Goleta, CA (US); Lois Jovanovic, Santa Barbara, CA (US); Howard Zisser, Santa Barbara, CA (US)

(72) Inventors: Francis J. Doyle, III, Santa Barbara, CA (US); Benyamin Grosman, Northridge, CA (US); Eyal Dassau, Goleta, CA (US); Lois Jovanovic, Santa Barbara, CA (US); Howard Zisser, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 1078 days.

(21) Appl. No.: 13/854,963

(22) Filed: Apr. 2, 2013

(65) Prior Publication Data

US 2013/0231642 A1    Sep. 5, 2013

Related U.S. Application Data

(63) Continuation of application No. PCT/US2011/056022, filed on Oct. 12, 2011.

(60) Provisional application No. 61/392,399, filed on Oct. 12, 2010.

(51) Int. Cl.
*A61M 31/00*     (2006.01)
*G06F 19/00*     (2011.01)
*G01N 33/66*     (2006.01)
*G01N 33/74*     (2006.01)

(52) U.S. Cl.
CPC .......... *A61M 31/002* (2013.01); *G01N 33/66* (2013.01); *G01N 33/74* (2013.01); *G06F 19/3437* (2013.01); *G06F 19/3468* (2013.01); *G01N 2333/62* (2013.01)

(58) Field of Classification Search
CPC ..... A61M 31/002; G01N 33/66; G01N 33/74; G01N 2333/62; G06F 19/3437; G06F 19/3468
USPC ......... 604/65–67, 131, 151; 128/DIG. 1, 12, 128/13; 600/301, 365
See application file for complete search history.

(56) References Cited

U.S. PATENT DOCUMENTS

| 2009/0192366 A1* | 7/2009 | Mensinger ........... A61B 5/0031 600/301 |
| 2009/0192380 A1* | 7/2009 | Shariati ................ A61B 5/0031 600/365 |
| 2009/0192745 A1* | 7/2009 | Kamath ............... A61B 5/0031 702/85 |
| 2010/0137788 A1 | 6/2010 | Braithwaite |

OTHER PUBLICATIONS

Benyamin Grosman et al. Zone Model Predictive Control: A Strategy to Minimize Hyper- and Hypoglycemic Events, Journal of Diabetes Science and Technology, Jul. 2010, 961-975.
(Continued)

*Primary Examiner* — Manuel Mendez
(74) *Attorney, Agent, or Firm* — Richard Aron Osman

(57) ABSTRACT

The disclosure relates to drug delivery and maintaining multiple defined physiological zones using model predictive control.

20 Claims, 5 Drawing Sheets

(56) References Cited

OTHER PUBLICATIONS

International Search Report and Written Opinion in PCT/US11/56022.
Information Disclosure Statement of U.S. Appl. No. 13/026,161.

* cited by examiner

MAINTAINING MULTIPLE DEFINED PHYSIOLOGICAL ZONES USING MODEL PREDICTIVE CONTROL

CROSS REFERENCE TO RELATED APPLICATIONS

This application claims priority from PCT/US11/56022, filed Oct. 12, 2011, and from U.S. Ser. No. 61/392,399, filed Oct. 12, 2010, the disclosure of which is incorporated herein by reference.

STATEMENT AS TO FEDERALLY SPONSORED RESEARCH

This invention was made with Government support under Grant No. ROI-DK085628-01 awarded by the National Institutes of Health. The U.S. Government has certain rights in this invention.

TECHNICAL FIELD

The disclosure relates to maintaining multiple defined physiological zones using model predictive control.

BACKGROUND

People with type 1 diabetes mellitus (T1DM) may have a life expectancy ten years less than their normal glucose tolerant counterparts due to complications resulting from chronic hyperglycemia, such as cardiovascular disease and strokes (hyperglycemia is an elevated blood glucose (BG) concentration, with a threshold defined as BG greater than 180 mg/dL). Aggressive treatment with intensive insulin therapy (IIT), involving up to a total of 12 manual capillary glucose measurements and insulin injections per day, reduces hyperglycemia and can lead to a reduction in the prevalence of these complications. IIT also increases the risk of hypoglycemic events and increases the burden on the caregiver and/or patient administering the therapy. Hypoglycemia is any lower than normal BG; symptoms of hypoglycemia, such as tachycardia and nausea, occur at around 50-70 mg/dL.

SUMMARY

Two of the challenges in designing an artificial pancreatic (β-cell are minimizing user intervention and fitting glucose targets to individual lifestyle and comfort. The disclosure provides a multiple zone model predictive control (Multi-Zone-MPC) with insulin and meal memory as a control approach that is engineered to regulate glucose into the euglycemia range by applying a control algorithm that incorporates tuning that is a function of the predicted blood glucose concentrations.

A Multi Zone-MPC controller with embedded artificial insulin and meal memory is developed to regulate blood glucose to a predefined tunable zone with or without meal information. The controller uses an average model to regulate the population's blood glucose concentrations. The average model is obtained by a novel parametric fitting technique that uses data that is collected from several of subjects. The controller tunings are predefined to be a function of the predicted blood glucose concentrations.

Multi-Zone-MPC provides different tunings for the MPC weights based on four regional distribution of glycemia. The Multi-Zone-MPC comprises a hypoglycemia, normoglycemia, elevated glycemia, and hyperglycemia zones. Defining these four zones provides richer control tunings that result in safe and effective control. The controller predictions are based on an average ARX-model that is developed using data collected from a meal response of ten different in silico adult subjects. It should be noted that the number of zones in the design can be modified a priori without major change to the controller structure.

Multi-Zone-MPC with insulin memory is an alternative control strategy for the artificial pancreas. As a control approach Multi-Zone-MPC is superior to standard set-point control due to the minimization of pump activity and more concentrated control effort. The use of four control zones in the Multi-Zone-MPC has successfully proven to be a better control strategy that reduces the postprandial peaks and at the same time avoids any hypoglycemia due to efficient insulin administration, hence, providing effective and safe glucose regulation to individuals with T1DM.

The subject algorithm and controller are generally applicable to delivering alternative drugs and physiological interventions, particularly drugs and interventions associated with titratable physiological zones.

In one aspect then invention provides a protocol for controlling drug delivery comprising a multi-zone model predictive control (MPC) algorithm having a plurality of defined physiological zones, each with a different predefined control tuning.

In particular embodiments the algorithm provides: (a) a relatively conservative control action for a large deviation from a normal or desired zone, and (b) a relative aggressive control action for within the normal or desired zone.

In particular embodiments the protocol comprises a logic scheme as shown in FIG. 5, wherein the algorithm provides physiological zones (G) and control weights (Q and R) according to the following schedule: (i) $R_1 \gg R_a$, when $G \geq G_{m+1}$; (ii) $G_1$ is an undesired zone that requires aggressive action that will result with suspension of delivery, wherein $Q_1 \ggg $ than $Q_{2, 3, \ldots, m}$; (iii) desired zone, Q is zero; (iv) for a large deviation from the normal or desired zone $(G_m)$, $Q_m < Q_{m-1}$, but not zero, and $\ll$ than $Q_1$; wherein "$\gg$" means at least one order of magnitude greater; and "$\ggg$" means at least two orders of magnitude.

In particular embodiments the protocol comprises a logic scheme as shown in FIG. 5, wherein Q/R are defined as a, b, c and d for four physiological zones, and (i) a<b; (ii) b/a>1×10$^3$; (iii) c=0; and (iv) d>>>than a, b and c.

In particular embodiments the protocol comprises a logic scheme as shown in FIG. 5, wherein Q/R are defined as a, b, c and d for four physiological zones, and: (i) a is 2×10$^{-4}$; (ii) b is 2; (iii) c=0; and (iv) d is 2×10$^{10}$.

In particular embodiments the physiological zones are zones of blood glucose concentration, anesthesia, analgesia, blood pressure, heart rate, blood pH, temperature, or in vivo drug concentration. For example, automated blood pressure control can be achieved using intravenous nitoprusside, heart rate control using in intravenous beta blockers or calcium channel blockers, pH control using ventilator modulation, temperature control (e.g. during open heart surgery) using heating and cooling elements, etc. Hence, in addition to drugs, the protocols can be used to deliver modulatable physiological interventions, such as ventilation, electrical stimulation, heat, etc.

In particular embodiments the drug is a hormone, a blood glucose regulator (such as insulin, glucagon or amylin), an anesthetic (such as Barbiturates, e.g. Amobarbital, Methohexital, Thiamylal and Thiopental, Benzodiazepines, e.g. Diazepam, Lorazepam and Midazolam, Etomidate, Ketamine and Propofol), an analgesic (such as Alfentanil, Fentanyl, Remifentanil, Sufentanil, Buprenorphine, Butorphanol, Diamorphine, Hydromorphone, Levorphanol, Meperidine, Methadone, Morphine, Nalbuphine, Oxycodone, Oxymorphone and Pentazocine, a muscle relaxant (such as Succinylcholine, Decamethonium, Mivacurium, Rapacuronium, Atracurium, Cisatracurium, Rocuronium, Vecuronium, Alcuronium, Doxacurium, Gallamine, Metocurine, Pancuronium, Pipecuronium and Tubocurarine, a chemotherapeutic (such as alkylating agents, antimetabolites, anthracyclines, plant alkaloids, topoisomerase inhibitors), or a antihypertensive (such as diuretics, ACE inhibitors, angiotensin II receptor antagonists, beta blockers, calcium channel blockers, renin inhibitors and glyceryl trinitrates).

In particular embodiments the physiological zones are blood glucose concentration zones, the drug is insulin, and the algorithm provides: (a) a relative conservative control action for a elevated "hyperglycemia" zone; and (b) a relatively aggressive control action for a normal or near normal "euglycemia" zone.

In particular embodiments the physiological zones are blood glucose concentration zones, the drug is insulin, and the algorithm provides: (a) a relative conservative control action for a elevated "hyperglycemia" zone; (b) a relatively aggressive control action for a normal or near normal "euglycemia" zone; (c) control inaction for a normoglycemia zone, and (d) a control action that results in suspending insulin delivery for a hypoglycemia zone.

In particular embodiments the algorithm provides glycemia zones and control weights ratios ($Q_k$ and $R_k$) according to the following schedule:

| Zone | Glycemia zones | $Q_k/R_k$ |
|---|---|---|
| 1. | $\tilde{G}'_k > 180$ mg/dL | 2E−4 |
| 2. | $140 < \tilde{G}'_k \leq 180$ mg/dL | 2 |
| 3. | $80 \leq \tilde{G}'_k \leq 140$ mg/dL | 0 |
| 4. | $\tilde{G}'_k < 80$ mg/dL | 2E10 | wherein in zone 1 ($\tilde{G}'_k > 180$ mg/dL) control actions are restrained to prevent over-dosing; in zone 2 ($140 < \tilde{G}'_k \leq 180$) most of the control actions are implemented; in zone 3 ($80 \leq \tilde{G}'_k \leq 140$) the controller is quiescent to deviation in glucose measurements; and in zone 4 ($\tilde{G}'_k < 80$) the controller is allowed to respond relatively fast to potential hypoglycemia.

In another aspect the invention provides a preferably non-transitory computer readable medium encoded with instructions for the subject protocols.

In another aspect the invention provides a drug delivery controller comprising an input contact, an output contact, and a multi-zone model predictive control (MPC) algorithm having a plurality of defined physiological zones, each with a different predefined control tuning, wherein the algorithm processes an input signal from a physiological sensor at the input contact to form an output signal to a drug infuser at the output contact, preferably wherein the physiological zones are blood glucose concentration zones, the drug is insulin, and the algorithm provides: (a) a relative conservative control action for a elevated "hyperglycemia" zone; and (b) a relatively aggressive control action for a normal or near normal "euglycemia" zone.

The controller may further comprise the physiologic sensor and/or the drug infuser, such as a glucose sensor and an insulin infuser or pump.

In another aspect the invention provides a method of delivering a drug comprising: (a) sensing a physiological metric with a sensor and receiving the resultant signal at the input contact of a subject controller; (b) processing the input signal to form the output signal; (c) transmitting the output signal from the output contact to an drug infuser; and (d) delivering the drug from the infuser pursuant to the output signal.

In another aspect the invention provides a method of delivering insulin comprising: (a) sensing blood glucose concentration with a glucose sensor and receiving the resultant signal at the input contact of a subject controller; (b) processing the input signal to form the output signal; (c) transmitting the output signal from the output contact to an insulin infuser; and (d) delivering insulin from the infuser pursuant to the output signal.

In another aspect the invention provides a method of delivering a drug, comprising: (a) obtaining drug and event data for a subject using an open loop protocol to obtain time values, drug values and physiological metric values; (b) defining a plurality of physiological zones as a function of physiological metric values; and (c) programming an automated drug pump comprising a controller having a multi-zone-model predictive control (MPC) algorithm, wherein the controller obtains physiological metric measurements from the subject, compares the physiological metrics to the plurality of physiological zones and causes delivery of the drug to the subject pursuant to the MPC algorithm.

In another aspect the invention provides a method of delivering insulin, comprising: (a) obtaining insulin and meal data for a subject using an open loop protocol to obtain time values, insulin values and glucose values; (b) defining a plurality of glycemia zones as a function of blood glucose concentration; and (c) programming an automated insulin pump comprising a controller having a multi-zone-model predictive control algorithm, wherein the controller obtains glucose measurements from the blood, compares the glucose values to the plurality of glycemia zones and causes delivery of insulin to the subject, particularly wherein the plurality of zones is set forth in Table 1.

In another aspect the invention provides a method of delivering a drug comprising: (a) determining physiological metric values from the blood of a subject; (b) comparing the physiological metric values to a plurality of defined physiological zones defined as a function of the physiological metric; and (c) automatically delivering the via a drug pump comprising a controller having a multi-zone-model predictive control (MPC) algorithm comprising the physiological zones.

In another aspect the invention provides a method of delivering insulin comprising: (a) determining glucose values from the blood of a subject; (b) comparing the glucose values to a plurality of defined glycemia zones defined as a function of blood glucose concentration; and (c) automatically delivering insulin or insulin analog via an insulin pump comprising a controller having a multi-zone-model predictive control algorithm comprising the glycemia zones.

In another aspect the invention provides a method of continuous monitoring and delivery of a drug to a subject. The method comprises obtaining values associated with blood levels of a drug for a subject; mapping the data using a transfer function; generating a linear difference model comprising a plurality of states; obtaining a plurality of defined value zones for the drug or biological agent in the subject; calculating a next administration dose and/or time of delivery of the drug based on a predicted drug value using the linear difference model and the defined zones; delivering the drug or biological agent to the subject based upon the calculated next administration. The recited drug may be drug metabolite or byproduct or induced factor. The value can be the blood concentration of the drug or a physiological metric or symptom (e.g., temperature).

Generally the invention encompasses embodiments substantially described herein above with reference to the specification and figures, and all combinations and subcombinations of particular embodiments as though each had been laboriously recited.

The details of one or more embodiments of the invention are set forth in the accompanying drawings and the description below. Other features, objects, and advantages of the invention will be apparent from the description and drawings, and from the claims.

DETAILED DESCRIPTION OF PARTICULAR EMBODIMENTS

Figure 1:
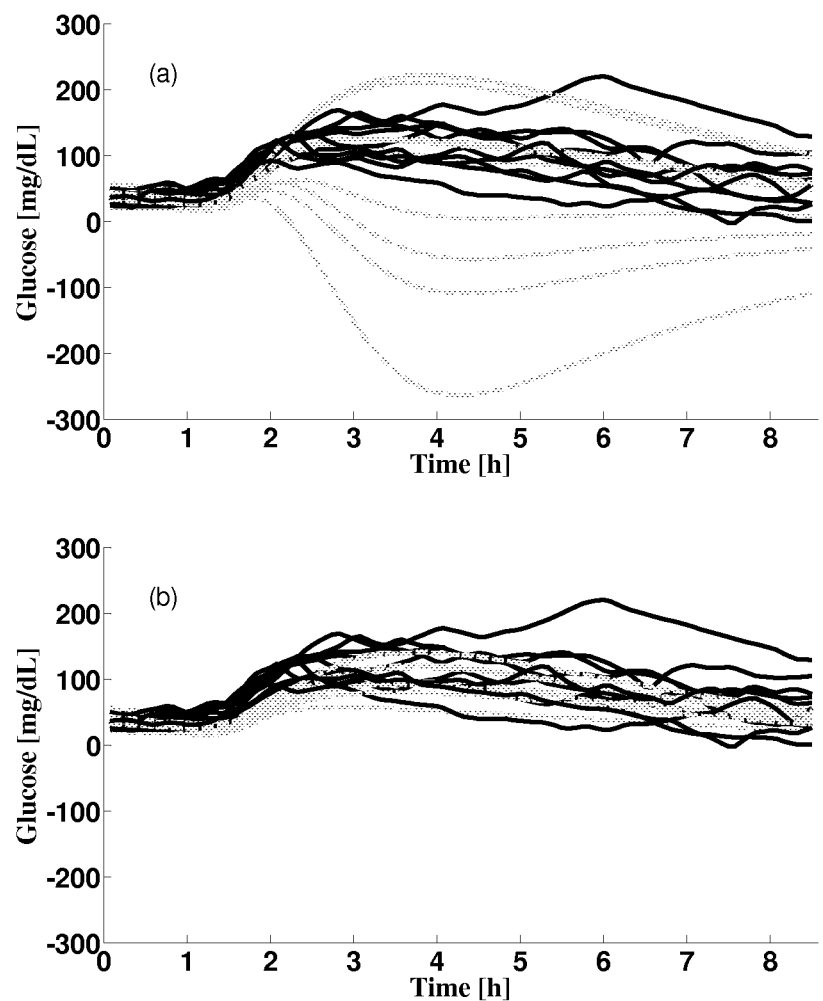
FIG. 1 shows prediction trajectories of the average model (grey lines) compared to the 10 in silico subjects (black lines). Panels (a) and (b) depict the initial guess for the optimization and the final optimization result, respectively. The initial guess of model (a) is generated by averaging the ARX individualized models population. The optimized average model (b) is obtained by a nonlinear optimization that was conducted on the population response. The population responses were obtained for the scenario of one 75 g meal scenario given at 1 hour of simulation time accompanied by an insulin bolus that was calculated by each subject insulin to carbohydrate ratio (I:C).

As used herein and in the appended claims, the singular forms "a," "and," and "the" include plural referents unless the context clearly dictates otherwise. Thus, for example, reference to "a device" includes a plurality of such devices and reference to "the pump" includes reference to one or more pumps and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The attraction of an automated system to control glucose and insulin levels would improve patient care and compliance. Thus, an efficient closed-loop device is thus threefold: increased life expectancy, decreased hypoglycemia, and reduction in the burden of administering effective therapy. Innovations in real-time continuous glucose monitoring (CGM) sensors and continuous subcutaneous insulin infusion (CSII) pumps mean that the components necessary for a closed-loop device suitable for use in ambulatory conditions are maturing, leaving the control algorithm as the limiting factor in development.

CGM sensors and CSII pumps use the subcutaneous (SC) route for glucose measurement and insulin delivery, respectively. Other routes, such as intravenous and intraperitoneal, offer reductions in lag time, but are associated with an increase in the risk of infection at the site of insertion. The lag time associated with SC insulin infusion is an obstacle for a control algorithm: absorption of glucose into the blood from carbohydrate (CHO) raises BG faster than simultaneously injected SC insulin can lower it. Insulin delivery rates may also be limited by the physical limitations of the CSII pump and safety constraints driven by clinical parameters. A controller framework known to be suitable for systems with large lag times and constraints is model predictive control (MPC). Central to each of these MPC implementations has been a dynamic model of the effects of subcutaneous insulin on glycemia.

The metabolic processes underlying insulin action involve complex interactions of hormones, which lead to significant variation in insulin sensitivity. Insulin absorption variability is less than insulin action variability, but can be affected by biofilms and inflammation. Gut glucose absorption is highly dependent upon the composition of a meal. Tracer studies involving radioactive isotopes have been reported in order to characterize subcutaneous insulin and gut glucose absorption; such models may be representative of the variation inherent in a population, but are not practical for use in an MPC algorithm because adapting these models to an individual subject would require the repetition of an expensive experiment. The use of data driven, empirical models based only on data collected from ambulatory subjects is a more practical method for development of a personalized model. The main caveat of developing models from data obtained from ambulatory subjects is that typically both model inputs—SC insulin and oral CHO—occur simultaneously, which gives an identifiability problem; the "best" empirical models can therefore have physically counterintuitive characteristics, such as an incorrect sign for a process gain. Classic process control techniques, such as impulse response tests, have been executed in clinical trials in which insulin boluses and meals were separated by 3 hours, and support the notion that a simple model—with a gain, a time constant, and a time delay—can capture the critical bandwidth behavior of glucose-insulin interactions.

Basal—bolus insulin treatment or intensive insulin treatment can be administered as multiple daily injections (MDI) or via an insulin pump (Skyler, 2005). Different insulin schedules are suggested for MDI therapy based on the insulin type and duration of action, the daily schedule of the patient, and other medical conditions. Initial doses are calculated based on body weight and are divided into basal and bolus partitions. However, since insulin requirements differ throughout the day, and from day to day, this initial setting needs to be fine tuned to prevent insulin overdose that will result in hypoglycemia or underdose that will result in hyperglycemia (Skyler, 2005). Insulin therapy using continuous subcutaneous insulin infusion (CSII) has become common practice since its introduction in 1978 (Pickup et al., 1978). CSII allows a continuous administration of rapid-acting insulin, with patient-activated boluses at mealtimes. This feature introduces a more physiological insulin administration, and therefore better glycemic control than MDI (Danne et al., 2008). CSII treatment depends on patient decisions and on pre-estimated basal therapy that can result in suboptimal treatment, and therefore a closed-loop algorithm becomes an appealing alternative.

The development of an artificial pancreatic β-cell started nearly four decades ago. These devices can be described as external or internal closed-loop systems that use continuous glucose measurements to manipulate insulin administration, and therefore compensate for the loss of natural abilities for glucoregulation of people with T1DM. First attempts to produce an artificial pancreas were made by Albisser et al. (1973) and Pfeiffer et al. (1974) using both venous blood glucose measurements and intravenous insulin administration. Clemens et al. (1982) used a clamping algorithm with the Biostator® Glucose-Controlled Insulin-Infusion System (GCIIS) and tested it in both animals and humans. Much later, Steil et al. (2004) used proportional integral derivative control (PID) for insulin administration.

Physicians are calculating "gains" through interactions with their patients with T1DM, and these clinical parameters are the standard of care in endocrinology practices. The "correction factor" (CF) is the lowering effect of BG from administering one unit of rapid-acting insulin; the "insulin-to-carbohydrate ratio" (ICR) is the amount of carbohydrate offset by one unit of rapid-acting insulin. These parameters are used to guide insulin dosing decisions and are often refined throughout the life of the person with T1DM. Due to this refinement process, the parameters obtained are considered reliable and should be included as a safety constraint in a closed-loop control algorithm.

Constrained MPC can necessitate the on-line solution of a quadratic program. This on-line optimization can be replaced with a single set of a priori optimizations via multi-parametric programming; the on-line problem is reduced to the evaluation of an affine function obtained from a lookup table. This reformulation is valuable in any application where on-line computation should be minimized, due to low computational power, or in order to extend battery life by minimizing computation, or to minimize the footprint on a chip.

In a classical implementation of multi-parametric programming, a quadratic program is solved online at each time-step; however, when a multi-parametric formulation of the problem is used, one optimization is performed offline, resulting in the evaluation of an affine function obtained from a lookup table as the only online computation necessary. Lookup table evaluation requires fewer online calculations and hence can contribute to extended battery life of the implementing device.

Model predictive control (MPC) is a computer control algorithm that uses an explicit process model to optimize future process response by manipulating future control moves (CM). The MPC concept was developed in the early 1970's and was referred to as identification and control (IDCOM) or as dynamic matrix control (DMC) by Shell engineers. Although MPC was originally implemented in petroleum refineries and power plants, it can be found these days in wide variety of application areas including aerospace, food, automotive and chemical applications. The most significant of the reasons for the popularity of MPC includes its handling of constraints, it accommodation of nonlinearities, and its ability to formulate unique performance criteria.

MPC optimizes every control cycle with a cost function that includes P future process instants, known as prediction horizon, and M future CM, the control horizon. In each cycle, the optimization is repeated using updated process data. However, only the first CM of each optimized sequence is sent to the process. Process inputs and outputs constraints are included directly such that the optimum solution prevents future constraint violation.

The different MPC algorithms can be classified into four approaches to specify future process response: fixed set point, zone, reference trajectory, and funnel. Using a fixed set point for the future process response can lead to large input adjustments unless the controller is detuned. A zone control is designed to keep the controlled variable (CV) in a zone defined by upper and lower boundaries that are usually defined as soft constraints. Some MPC algorithms define a desired response path for the CVs, called reference trajectory. The reference trajectory usually describes a define path from current CV state to a desired set point. The reference trajectory control returns to a fixed set-point control when the CV approaches the defined set point. The Robust Multivariable Predictive Control Technology (RM-PCT, Honeywell Inc., 1995) attempts to keep the CV in a defined zone; however, when the CV is out of the zone, a funnel is defined to bring the CV back into the zone.

The disclosure utilizes a lookup table defining zones of glycemia. In one embodiment, the lookup table comprises two zones (e.g., a hypoglycemia zone and a hyperglycemia zone). In another embodiment, the table comprises 3 or 4 zones. The zones are defined by blood glucose values (see Table 1, below). In other embodiments, physiological measurements of a subject to define a lookup table using carbohydrate consumption and insulin delivery (e.g., delivery subcutaneously) are used. The look up table can take in to account risk constraints such as insulin-on-board measurements and the like. Once a set of measurements are made a look up table is defined including parameters.

A number of different models for generating a lookup table are described below. As shown in the drawings for purposes of illustration, the invention is embodied in a closed loop infusion system for regulating the rate of fluid infusion into a body of a user based on feedback from an analyte concentration measurement taken from the body. In particular embodiments, the disclosure is embodied in a control system for regulating the rate of insulin infusion into the body of a user based on a glucose concentration measurement taken from the body.

The system is based in part upon a lookup table development using various models of glucose and insulin measurements and predictions. Accordingly, a method of the disclosure includes first making measurements of a body system in response to food/glucose/carbohydrate adsorption and insulin delivery and insulin-on-board measurements. These measurements are then modeled to the subject's metabolic system and a controller is ultimately programmed to include a look up table that relates insulin and glucose measurements as well as accepted or calculated glycemic zones (e.g., zone defining a low and high threshold for blood glucose corresponding to, for example, hypoglycemia, hyperglycemia and the like).

A typical insulin delivery device of the disclosure comprises a sensor system for measuring glucose and/or insulin, a controller and an insulin delivery system. The glucose sensor system generates a sensor signal representative of blood glucose levels in the body, and provides the sensor signal to the controller. The controller receives the sensor signal and generates commands that are communicated to the insulin delivery system. The insulin delivery system receives the commands and infuses insulin into the body in response to the commands.

Generally, the glucose sensor system includes a glucose sensor, sensor electrical components to provide power to the sensor and generate the sensor signal, a sensor communication system to carry the sensor signal to the controller, and a sensor system housing for the electrical components and the sensor communication system.

Typically, the controller includes controller electrical components and software to generate commands for the insulin delivery system based on the sensor signal, and a controller communication system to receive the sensor signal and carry commands to the insulin delivery system.

Generally, the insulin delivery system includes an infusion device and an infusion tube to infuse insulin into the body. In particular embodiments, the infusion device includes infusion electrical components to activate an infusion motor according to the commands, an infusion communication system to receive the commands from the controller, and an infusion device housing to hold the infusion device.

The controller is housed in the infusion device housing and the infusion communication system is an electrical trace or a wire that carries the commands from the controller to the infusion device. In alternative embodiments, the controller is housed in the sensor system housing and the sensor communication system is an electrical trace or a wire that carries the sensor signal from the sensor electrical components to the controller electrical components. In other alternative embodiments, the controller has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces.

The following examples are intended to illustrate but not limit the disclosure. While they are typical of those that might be used, other procedures known to those skilled in the art may alternatively be used.

EXAMPLES

Example 1

In recent years, model predictive control (MPC) has been shown to be a promising direction for an artificial pancreas control algorithm (Parker et al., 1996). MPC is an optimal control algorithm that has been used in the chemical process industries over the last four decades. It is based on a computer control algorithm that uses an explicit process model to optimize future process response by manipulating future control moves (CM). The MPC concept was developed in the early 1970's and was referred to as identification and control (IDCOM) (Richalet et al., 1976) or as dynamic matrix control (DMC) by engineers from the Shell Company (Cutler and Ramaker, 1979). Although MPC was originally implemented in petroleum refineries and power plants, it can be found these days in wide variety of application areas including aerospace, food, automotive and chemical applications (Qin and Badgwell, 2003). Among the reasons for the popularity of MPC are its handling of constraints, it accommodation of nonlinearities, and its ability to formulate unique performance criteria.

Zone-MPC that is described in Grosman et al. (2010) contains a zone of normoglycemia in which the control is not responding to variations in glycemia, and regions surrounding this zone that are controlled with a fixed setting. Zone-MPC showed significant advantages over the "optimal" open-loop therapy, and it has shown the reduction of control moves variability with minimal loss of performance compared to set-point control.

In this work we present an artificial pancreatic β-cell based on Multi-Zone-MPC. The discussed control algorithm is based on four glycemia zones that are regulated with different control tunings. The controller is based on a single model resulting from an average patient ARX-model.

The response of ten in silico adult subjects, using the FDA-accepted UVa\Padova metabolic simulator (Kovatchev et al., 2009), is obtained from a single meal of 75 g of carbohydrates. The meal-related insulin bolus is calculated automatically by the simulator based on subject specific insulin to carbohydrate ratio. The continuous glucose monitor (CGM) data is collected for eight hours and twenty minutes and used for individualized identification of part (a) of (1) by linear regression (Ljung, 1999). Parts (b), and (c) of (1) are kept constant for all subjects. This identification is described in detail in Grosman et al. (2010). The following equation represents the general average model structure:

$$\begin{aligned}&(a)\\&\tilde{G}'_k = \alpha_1 G'_{k-1} + \alpha_2 G'_{k-2} + \ldots + \alpha_5 G'_{k-5} \ldots + \beta_1 I_{Mk-1} + \beta_2 I_{Mk-2} + \ldots + \\&\qquad \beta_{11} I_{Mk-11} \ldots + \chi_1 M_{Mk-1} + \chi_2 M_{Mk-2} + \ldots + \chi_{11} M_{Mk-11}\\&\tilde{G}_k = \phi \cdot \theta^T\\&\text{where}\\&\phi = [\, G_{k-1} \ldots G_{k-5} \quad I_{Mk-1} \ldots I_{Mk-11} \quad M_{Mk-1} \ldots M_{Mk-11} \,]\\&\text{and}\\&\theta = [\, \alpha_1 \ldots \alpha_5 \quad \beta_1 \ldots \beta_{11} \quad \chi_1 \ldots \chi_{11} \,]\\&(b)\\&I_M(k) = 1.665 I_M(k-1) - 0.693 I_M(k-2) \ldots + \\&\qquad\qquad\qquad 0.01476 I'_D(k-1) + 0.01306 I'_D(k-2)\\&(c)\\&M_M(k) = 1.501 M_M(k-1) + 0.5427 M_M(k-2) \ldots + \\&\qquad\qquad\qquad 0.02279 M'(k-1) + 0.01859 M'(k-2)\end{aligned} \qquad (1)$$

where, $\tilde{G}'_k$ mg/dL is the estimation of the blood glucose concentration in deviation variable ($\tilde{G}'_k = \tilde{G}_k - 110$ mg/dL) at time k, $I_M$ U/h is the mapped subcutaneous insulin infusion rate, $M_M$ g is the mapped carbohydrate (CHO) ingestion input, $I_D'$ U/h is the insulin infusion rate in deviation variable ($I_D'=I_D$–basal U/h), and M g is the CHO ingestion input. θ is the regression vector, and α, β, and χ are the glucose, the insulin, and meal regressors, respectively.

An initial guess for the average model is obtained by averaging the ten different vectors θ of (1) that are obtained from the identification of part (a) of (1) for each patient separately. Accuracy of the initial average model is illustrated in FIG. 1(a) and shows limited predictability for some subjects.

Next, nonlinear optimization, (2), is conducted to reduce the sum square of errors (SSE) between the average model's prediction for a period of eight hours and twenty minutes and the raw data collected from each subject.

$$\min_\theta \left\{ \sum_{k=1}^{PH} (\tilde{G}_k' - G_k')^2 \right\} \quad (2)$$

where PH is the prediction horizon of eight hours and twenty minutes. The optimization is carried out under the following constraints:

1. For stability and anti-aliasing, the roots of the characteristic polynomial, $z^5-\alpha_1 z^4-\alpha_2 z^3-\alpha_3 z^2-\alpha_4 z^1-\alpha_5$, are all inside the right-hand side (RHS) of the unit circle. Where $\alpha_{1-5}$ are the glucose auto regressors as described in (1).

2. Negative insulin gain requirement, $$\frac{\sum_{i=1}^{11} \beta_i}{1 - \sum_{j=1}^{5} \alpha_j} < 0.$$

Where $\alpha_{1-5}$, $\beta_{1-11}$ are the glucose and insulin regressors, respectively described in (1).

3. Positive meal gain requirement, $$\frac{\sum_{i=1}^{11} \chi_i}{1 - \sum_{j=1}^{5} \alpha_j} > 0.$$

Where $\alpha_{1-5}$, $\chi_{1-11}$ are the glucose and meal regressors, respectively as described in (1).

4. No inverse response in insulin and meal. This is achieved by constraining all $\beta_i \geq 0$ and all $\chi_i \leq 0$.

The optimization result is depicted in FIG. 1(b) and describes a model that captures the general behavior of the 10 subjects population.

MPC optimizes every control sample with a cost function that includes P future process instants, known as the prediction horizon, and M future CM, the control horizon. In each sample, the optimization is repeated using updated process data. However, only the first CM of each optimized sequence is implemented on the process. Process input constraints are included such that the optimum solution prevents future constraint violation.

Guided by medical practice, the blood glucose concentration can be divided into four zones: zone 1, hyperglycemia, BG>180 mg/dL; zone 2, near normal glycemia, 140<BG<180 mg/dL; zone 3, normoglycemia, 80<BG<140 mg/dL, and zone 4, danger of imminent hypoglycemia, BG<80 mg/dL. These zones are included into the cost function used in the Multi-Zone-MPC that is described by the following equation:

$$J(u) \sum_{k=1}^{P} \|(\tilde{G}_k' - G_k^r)\| Q_k \ldots + \sum_{k=0}^{M-1} \|I_{Dk}'\| R_k \quad (3)$$

s.t.
$$\tilde{G}_{k+1}' = f(\tilde{G}_k, I_{Dk}') \; \forall \; k = 1, P$$
$$I_{min} \leq I_{Dk}' \leq I_{max} \; \forall \; k = 1, M$$

where $G_k^r$ is a binary function that yields the values of the upper bound of the normoglycemia zone (140 mg/dL) when $\tilde{G}_k'>140$ mg/dL, and yield the values of the lower bound of the normoglycemia zone (80 mg/dL) when $\tilde{G}_k'<80$ mg/dL. $Q_k$ and $R_k$ are predicted blood glucose concentration dependent optimization weights as listed in Table 1. P and M are the output prediction horizon, and control horizon, respectively.

The Multi-Zone-MPC predicts P steps in every control sample. $Q_k$ and $R_k$ switch values according the predictions. If $80 \leq \tilde{G}_k' \leq 140$ then $Q_k$ is set to zero. If $\tilde{G}_k'>180$ mg/dL for at least a single prediction then $Q_k$ and $R_k$ are switched to $Q_k=1$ and $R_k=5000$. Otherwise, $R_k=0.5$ for all prediction and $Q_k$ switches according to each $\tilde{G}_k'$ value.

TABLE 1

Multi-Zone-MPC weights as function of blood glucose concentration

| Zone | Glycemia zones | $Q_k/R_k$ |
|---|---|---|
| 1. | $\tilde{G}_k' > 180$ mg/dL | 2E–4 |
| 2. | $140 < \tilde{G}_k' \leq 180$ mg/dL | 2 |
| 3. | $80 \leq \tilde{G}_k' \leq 140$ mg/dL | 0 |
| 4. | $\tilde{G}_k' < 80$ mg/dL | 2E10 |

Table 1 describes the various glycemic zones and the control weights ratio ($Q_k$ and $R_k$) used for the Multi-Zone-MPC. In zone 1 ($\tilde{G}_k'>180$ mg/dL) control actions are restrained to prevent over-dosing. In zone 2 ($140<\tilde{G}_k'\leq 180$) most of the control action are implemented. In zone 3 ($80 \leq \tilde{G}_k' \leq 140$) the controller is quiescent to deviation in glucose measurements. In zone 4 ($\tilde{G}_k'<80$) the controller is allowed to respond fast to potential hypoglycemia. The control saneness of the four glycemia zones is described by the following:

ZONE 1 ($\tilde{G}_k'>180$ mg/d/L). In this zone the control actions are restrained to prevent over-dosing. There are at least two good reasons to restrain the control actions in this zone. First, the controller predictions are based on a linear model that is reliable mainly around the linearization point (110 mg/dL). Therefore, inaccurate control action may results in regions that are remote from the linearization point. Second, the control actions are proportional to the deviation of the predicted blood glucose concentration from the bounds of the normoglycemia zone ($80 \leq \tilde{G}_k' \leq 140$), and therefore large control moves are anticipated when the prediction are far from these bounds. This can lead to insulin overdosing in the present of noise or model mismatch.

ZONE 2 ($140<\tilde{G}_k'180$). In this zone most of the control actions to avoid hyperglycemia are implemented. This zone is close enough to the upper bound of the normoglycemia zone and therefore a more liberated control action can be implemented.

ZONE 3 ($80 \leq \tilde{G}'_k 140$). Quiescent control zone, the controller does not respond to deviation in glucose measurements. This zone represents the normoglycemia and it is assumed that a subject glycemia can vary between the bounds of this zone without need for regulation.

ZONE 4 ($\tilde{G}'_k < 80$). In this zone the weight on the control actions is freed to enable a fast pump shutdown when needed, and by that, preventing pending hypoglycemia.

Comparison of Multi-Zone-MPC and Zone-MPC is conducted on 100 in silico adult subjects following a one meal scenario of 75 g of CHO given at 8 pm using the FDA-accepted UVa/Padova metabolic simulator. Control is enabled after two hours of open-loop response.

Magni et al. (2008) introduced the control variability grid analysis (CVGA) for measuring the quality of closed-loop glucose control on a group of subjects. It is a method for visualization of the extreme glucose excursions caused by a control algorithm in a group of subjects, with each subject presented by one data point for any given observation period. A numeric assessment of the overall level of glucose regulation in the population is given by the summary outcome of the CVGA.

Figure 2:
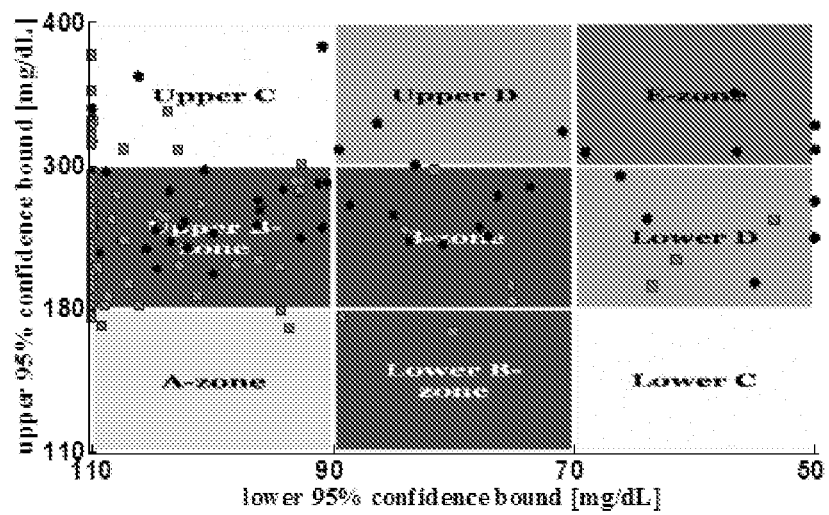
FIG. 2 shows a comparison between control variability grid analysis (CVGA) results of Multi-Zone-MPC (squares) and Zone-MPC (circles). As can be seen, Multi-Zone-MPC prevented four profound hypoglycemic events that are caused when Zone-MPC is used. Moreover, the maximum and minimum population glycemic extremum that are observed using the Multi-Zone-MPC are 391 and 52 mg/dL compared to 399 and 24 mg/dL obtained by the Zone-MPC.

FIG. 2 depicts the CVGA for the Multi-Zone-MPC and the Zone-MPC. As can be seen the Multi-Zone-MPC significantly reduces the risk of hypoglycemia and at the same time lowers the hyperglycemia levels.

Figure 3:
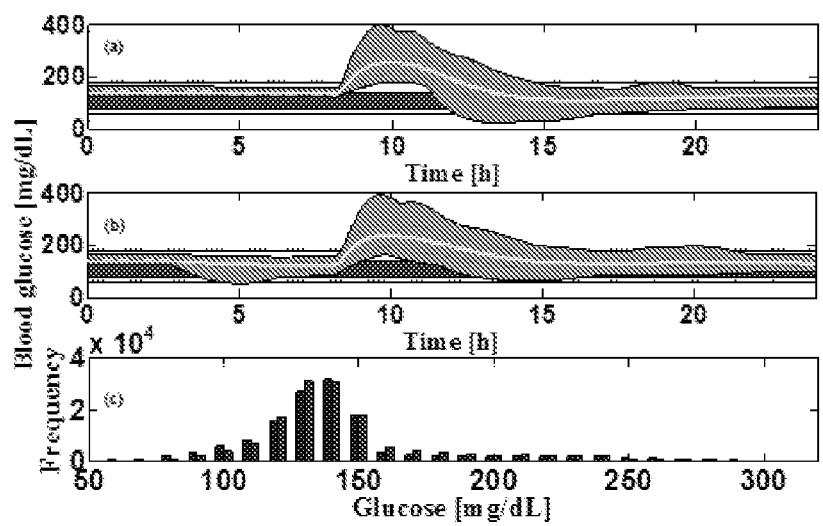
FIG. 3 shows a population responses of the Zone-MPC (a), Multi-Zone-MPC (b), and the histogram of the population glucose distribution (c). In panels (a) and (b) the zone $80 \leq G \leq 140$ is depicted by the darker grey area, and the two black horizontal lines depict G=180 mg/dL and G=60 mg/dL, respectively.

FIG. 3 describes the population response to the tested scenario on all 100 UVa\Padova metabolic simulator subjects. As can be seen, Multi-Zone-MPC outperforms the Zone-MPC with extended time in the near normal glucose range without any severe hypoglycemic events.

TABLE 2

Indices of performance summary.

| Average index | Multi-Zone-MPC | Zone-MPC |
|---|---|---|
| LBGI | 0.1 | 0.5 |
| HBGI | 4.2 | 4.3 |
| % time 80 ≤ G ≤ 180 | 83 | 81 |
| % time G ≥ 180 | 16 | 17 |
| # of subjects below 60 | 1 | 7 |

Table 2 summarizes a number of average indices of performance. First two rows present the low and the high blood glucose indices (LBGI, and HBGI) (Kovatchev et al., 2002), respectively. The LBGI and the HBGI are non-negative quantities that increases when the measurements of low or high blood glucose increases. These indices range is between 0 to 100, where low values indicate better glycemia regulation. The percentage of time the blood glucose concentration is between 80 to 180 mg/dL, and above 180 mg/dL are shown in the third and the fourth row, respectively. The fifth row presents the number of in silico subjects that experienced at least one hypoglycemic event. It can be seen that using the Multi-Zone-MPC approach reduces significantly the number hypoglycemic events from 7 to 1, and reduces the LBGI from 0.5 to 0.1, while introducing a lower HBGI and higher glycemic percentage of time between 80 and 180 mg/dL.

Figure 4:
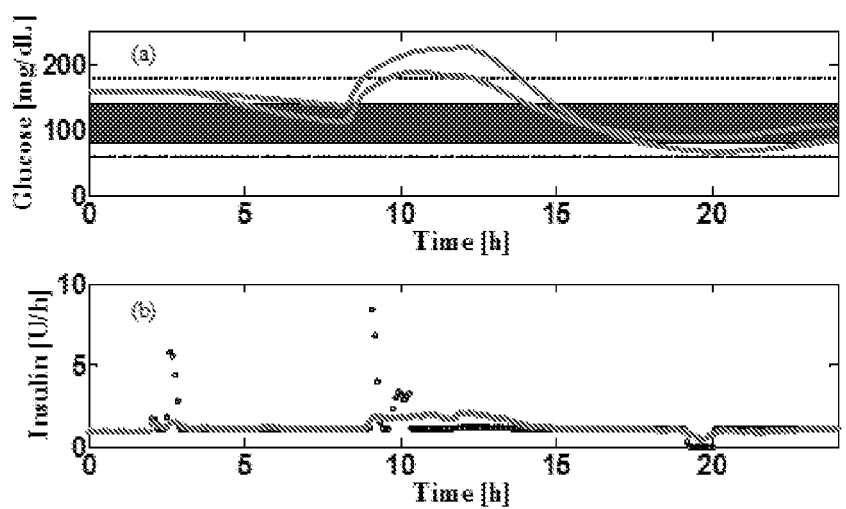
FIG. 4 shows A Subject response to one 75 g meal scenario given at 8 hours from the beginning of the simulation. The lower and higher curves represent the Multi-Zone-MPC and the Zone-MPC, respectively. Panels (a) and (b) are the glucose trajectories and the insulin control actions, respectively.

FIG. 4 shows a comparison of a subject's response to the Multi-Zone-MPC and Zone-MPC. One can see the advantage of Multi-Zone-MPC that significantly reduces the hyperglycemia values while keeping the glucose levels away from hypoglycemia.

A good illustration of the algorithm features is depicted in FIG. 4. The initial simulation values that are between $140 < \tilde{G}'_k \leq 180$ are regulated by rapid control action around the second hour of the evaluation as closed-loop is engaged. Around hour 8 a meal is given and the values of the predicted glycemia enter the $140 < \tilde{G}'_k \leq 180$ mg/dL zone. This deviation is been handled fast by two relative large boluses. The controller continues to regulate glycemia in a more conservative way when the predictions cross to the next zone $\tilde{G}'_k > 180$ mg/dL. Around hour 19 a shutdown of the pump is performed for 60 min to prevent pending hypoglycemia. On the other hand, the Zone-MPC is less efficient in both reducing the hyperglycemia peak and avoiding hypoglycemia with nadir glucose of ~65 mg/dL.

The CVGA results (FIG. 2) and the population results (FIG. 3) show that the Multi-Zone-MPC moves the extremum glycemia values to a lower hyperglycemia without reaching hypoglycemia. Table 2 also emphasizes that the Multi-Zone-MPC reduces significantly the number of hypoglycemic events from 7 to 1, and the LBGI from 0.5 to 0.1, while still manifesting better lower HBGI and higher percentage of time between 80 to 180 mg/dL. This indicates that the Multi-Zone-MPC can be safe and efficient at the same time.

Multi-Zone-MPC was evaluated on the FDA-accepted UVa/Padova metabolic simulator. The control was based on an average ARX-model that was identified in a novel approach by applying a nonlinear optimization with an initial guess based on ARX-models of different subjects. Multi-Zone-MPC showed significant advantages over Zone-MPC that was presented in previous work and showed to be superior to MPC with fixed setpoint. The separation of the control tuning into four zones allows at the same time an efficient and safe glycemia regulation. Since fixed tuning was used for the population it is expected that individualized tuning may improve the results even more.

A number of embodiments of the invention have been described. Nevertheless, it will be understood that various modifications may be made without departing from the spirit and scope of the invention. Accordingly, other embodiments are within the scope of the following claims.

What is claimed is:

1. A drug delivery controller comprising an input contact, an output contact, and a multi-zone model predictive control (MPC) algorithm having a plurality of defined physiological zones, each with a different predefined control tuning, wherein the algorithm processes an input signal from a physiological sensor at the input contact to form an output signal to a drug infuser at the output contact.

2. The controller of claim 1 wherein the algorithm provides:
   (a) a relatively conservative control action for a large deviation from a normal or desired zone, and
   (b) a relative aggressive control action for within the normal or desired zone.

Figure 5:
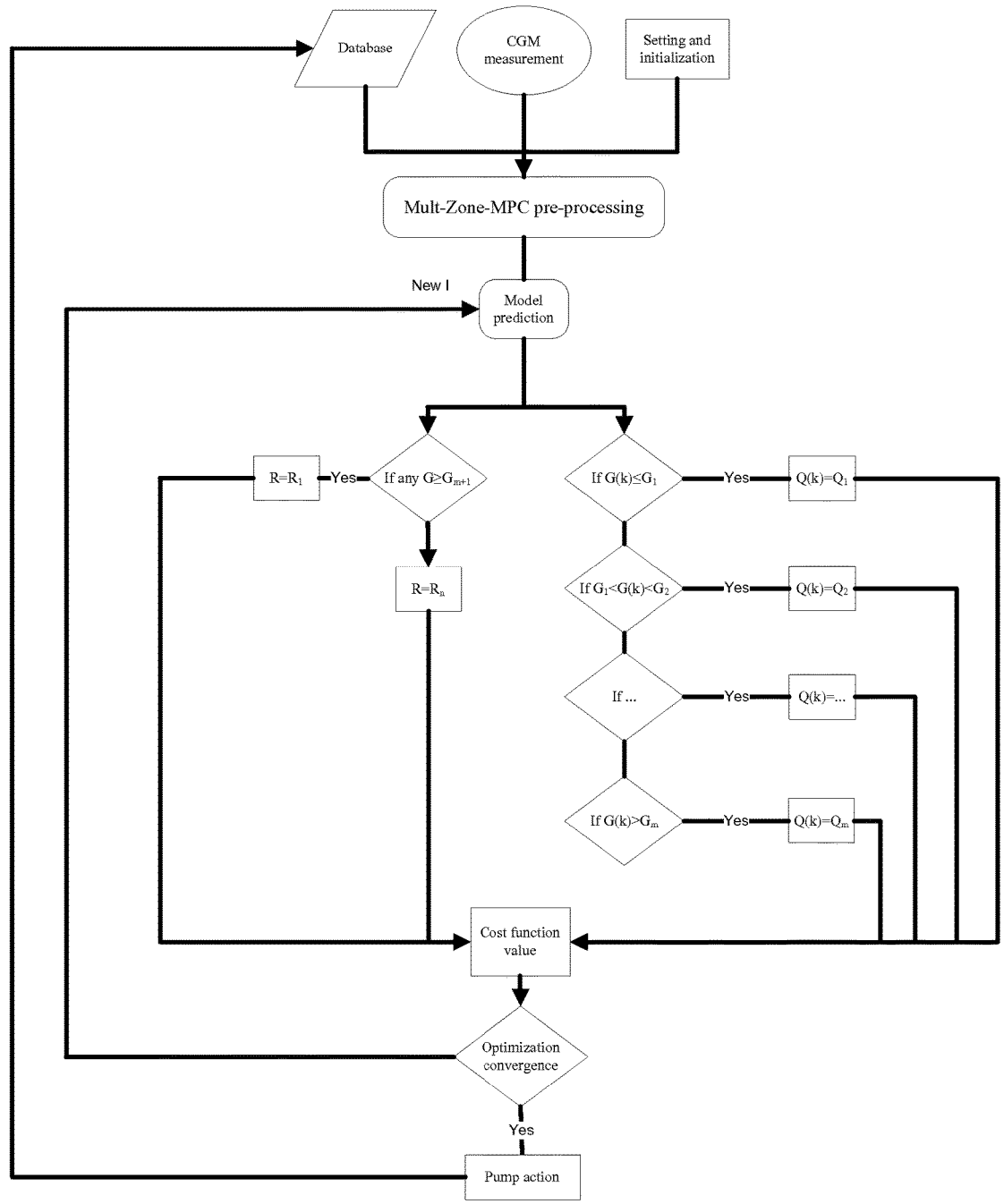
FIG. 5 shows a generic flow diagram of the Multi-Zone MPC.
Figure 6:
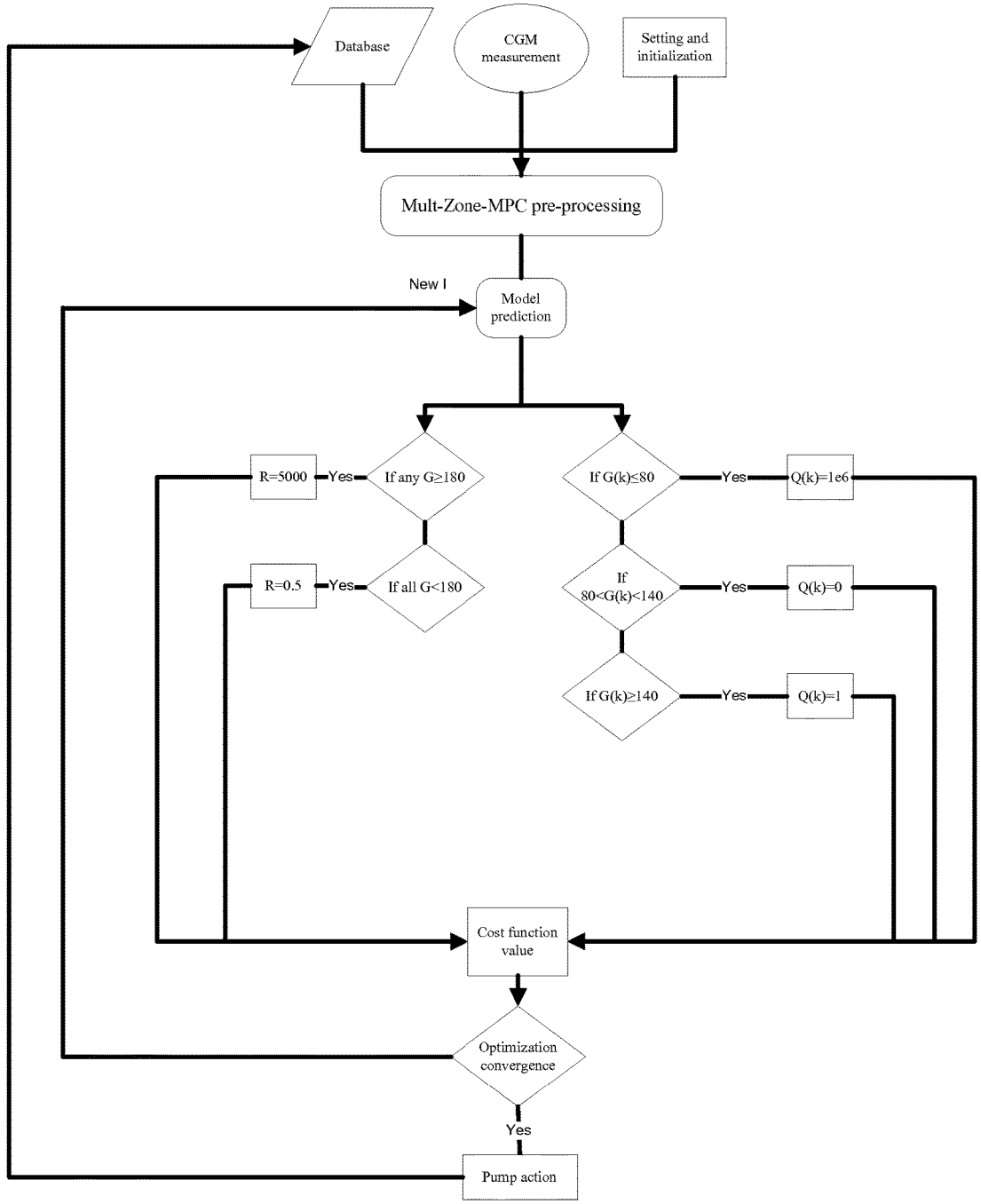
FIG. 6 shows a four zone example of the Multi-Zone MPC.

3. The controller of claim 1 comprising a logic scheme as shown in FIG. 5, wherein the algorithm provides physiological zones (G) and control weights (Q and R) according to the following schedule:
   (i) $R_1 \gg R_a$, when $G \geq G_{m+1}$;
   (ii) $G_1$ is an undesired zone that requires aggressive action that will result with suspension of delivery, wherein $Q_1 \ggg$ than $Q_{2, 3, \ldots, m}$;
   (iii) desired zone, Q is zero;
   (iv) for a large deviation from the normal or desired zone ($G_m$), $Q_m < Q_{m-1}$, but not zero, and $\ll$ than $Q_1$;

wherein ">>" means at least one order of magnitude greater; and ">>>" means at least two orders of magnitude.

4. The controller of claim 1 comprising a logic scheme as shown in FIG. 5, wherein Q/R are defined as a, b, c and d for four physiological zones, and:
   (i) a<b;
   (ii) b/a>1×10³;
   (iii) c=0; and
   (iv) d>>>than a, b and c.

5. The controller of claim 1 comprising a logic scheme as shown in FIG. 5, wherein Q/R are defined as a, b, c and d for four physiological zones, and:
   (i) a is 2×10⁴;
   (ii) b is 2;
   (iii) c=0; and
   (iv) d is 2×10¹⁰.

6. The controller of claim 1 wherein the physiological zones are blood glucose concentration zones, the drug is insulin, and the algorithm provides:
   (a) a relative conservative control action for a elevated "hyperglycemia" zone; and
   (b) a relatively aggressive control action for a normal or near normal "euglycemia" zone.

7. The controller of claim 1 wherein the physiological zones are blood glucose concentration zones, the drug is insulin, and the algorithm provides:
   (a) a relative conservative control action for a elevated "hyperglycemia" zone;
   (b) a relatively aggressive control action for a normal or near normal "euglycemia" zone;
   (c) control inaction for a normoglycemia zone; and
   (d) a control action that results in suspending insulin delivery for a hypoglycemia zone.

8. The controller of claim 1 wherein the algorithm provides glycemia zones and control weights ratios ($Q_k$ and $R_k$) according to the following schedule:

| Zone | Glycemia zones | $Q_k/R_k$ |
|---|---|---|
| 1. | $\tilde{G}'_k > 180$ mg/dL | 2E−4 |
| 2. | $140 < \tilde{G}'_k \leq 180$ mg/dL | 2 |
| 3. | $80 \leq \tilde{G}'_k \leq 140$ mg/dL | 0 |
| 4. | $\tilde{G}'_k < 80$ mg/dL | 2E10 | wherein in zone 1 ($\tilde{G}'_k > 180$ mg/dL) control actions are restrained to prevent over-dosing; in zone 2 ($140 < \tilde{G}'_k \leq 180$) most of the control actions are implemented; in zone 3 ($80 \leq \tilde{G}'_k \leq 140$) the controller is quiescent to deviation in glucose measurements; and in zone 4 ($\tilde{G}'_k < 80$) the controller is allowed to respond relatively fast to potential hypoglycemia.

9. The controller of claim 1 further comprising the physiologic sensor and the drug infuser.

10. The controller of claim 1 further comprising the physiologic sensor, which is a glucose sensor, and the drug infuser, which is an insulin infuser.

11. A method of delivering a drug comprising:
   (a) sensing a physiological metric with a sensor and receiving the resultant signal at the input contact of the controller of claim 1;
   (b) processing the input signal to form the output signal;
   (c) transmitting the output signal from the output contact to an drug infuser; and
   (c) delivering the drug from the infuser pursuant to the output signal.

12. A method of delivering insulin comprising:
   (a) sensing blood glucose concentration with a glucose sensor and receiving the resultant signal at the input contact of the controller of claim 1;
   (b) processing the input signal to form the output signal;
   (c) transmitting the output signal from the output contact to an insulin infuser; and
   (d) delivering insulin from the infuser pursuant to the output signal.

13. A method of delivering a drug, comprising:
   (a) obtaining drug and event data for a subject using an open loop protocol to obtain time values, drug values and physiological metric values;
   (b) defining a plurality of physiological zones as a function of physiological metric values; and
   (c) programming an automated drug pump comprising a controller having a multi-zone-model predictive control (MPC) algorithm,
   wherein the controller obtains physiological metric measurements from the subject, compares the physiological metrics to the plurality of physiological zones and causes delivery of the drug to the subject pursuant to the MPC algorithm.

14. A method of claim 13 of delivering insulin, comprising:
   (a) obtaining insulin and meal data for a subject using an open loop protocol to obtain time values, insulin values and glucose values;
   (b) defining a plurality of glycemia zones as a function of blood glucose concentration; and
   (c) programming an automated insulin pump comprising a controller having a multi-zone-model predictive control algorithm,
   wherein the controller obtains glucose measurements from the blood, compares the glucose values to the plurality of glycemia zones and causes delivery of insulin to the subject.

15. The method of claim 14, wherein the plurality of zones is set according to the following schedule:

| Zone | Glycemia zones | $Q_k/R_k$ |
|---|---|---|
| 1 | $\tilde{G}'_k > 180$ mg/dL | 2E−4 |
| 2 | $140 < \tilde{G}'_k \leq 180$ mg/dL | 2 |
| 3 | $80 \leq \tilde{G}'_k \leq 140$ mg/dL | 0 |
| 4 | $\tilde{G}'_k < 80$ mg/dL | 2E10 | wherein in zone 1 ($\tilde{G}'_k > 180$ mg/dL) control actions are restrained to prevent over-dosing; in zone 2 ($140 < \tilde{G}'_k \leq 180$) most of the control actions are implemented; in zone 3 ($80 \leq \tilde{G}'_k \leq 140$) the controller is quiescent to deviation in glucose measurements; and in zone 4 ($\tilde{G}'_k < 80$) the controller is allowed to respond relatively fast to potential hypoglycemia.

16. A method of delivering a drug comprising:
   (a) determining physiological metric values from the blood of a subject;
   (b) comparing the physiological metric values to a plurality of defined physiological zones defined as a function of the physiological metric; and
   (c) automatically delivering the via a drug pump comprising a controller having a multi-zone-model predictive control (MPC) algorithm comprising the physiological zones.

17. A method of claim 16 of delivering insulin comprising:

(a) determining glucose values from the blood of a subject;
(b) comparing the glucose values to a plurality of defined glycemia zones defined as a function of blood glucose concentration; and
(c) automatically delivering insulin or insulin analog via an insulin pump comprising a controller having a multi-zone-model predictive control algorithm comprising the glycemia zones.

18. The method of claim 16 wherein the algorithm provides:
(a) a relatively conservative control action for a large deviation from a normal or desired zone, and
(b) a relative aggressive control action for within the normal or desired zone.

19. The method of claim 16 wherein the physiological zones are blood glucose concentration zones, the drug is insulin, and the algorithm provides:
(a) a relative conservative control action for a elevated "hyperglycemia" zone;
(b) a relatively aggressive control action for a normal or near normal "euglycemia" zone;
(c) control inaction for a normoglycemia zone; and
(d) a control action that results in suspending insulin delivery for a hypoglycemia zone.

20. The method of claim 16 wherein the algorithm provides glycemia zones and control weights ratios ($Q_k$ and $R_k$) according to the following schedule:

| Zone | Glycemia zones | $Q_k/R_k$ |
|---|---|---|
| 1 | $\tilde{G}'_k > 180$ mg/dL | 2E−4 |
| 2 | $140 < \tilde{G}'_k \leq 180$ mg/dL | 2 |
| 3 | $80 \leq \tilde{G}'_k \leq 140$ mg/dL | 0 |
| 4 | $\tilde{G}'_k < 80$ mg/dL | 2E10 | wherein in zone 1 ($\tilde{G}'_k > 180$ mg/dL) control actions are restrained to prevent over-dosing; in zone 2 ($140 < \tilde{G}'_k \leq 180$) most of the control actions are implemented; in zone 3 ($80 \leq \tilde{G}'_k \leq 140$) the controller is quiescent to deviation in glucose measurements; and in zone 4 ($\tilde{G}'_k < 80$) the controller is allowed to respond relatively fast to potential hypoglycemia.

* * * * *